United States Patent [19]

Waller

[11] Patent Number: 4,746,686
[45] Date of Patent: May 24, 1988

[54] VISIBLE LIGHT ACTIVATED CAVITY LINER

[75] Inventor: Duncan E. Waller, Ypsilanti, Mich.

[73] Assignee: Kerr Manufacturing Company, Romulus, Mich.

[21] Appl. No.: 39,287

[22] Filed: Apr. 17, 1987

[51] Int. Cl.$^4$ .................. C08F 2/50; C08F 20/20; C08K 3/32; C08K 3/40

[52] U.S. Cl. .................................... 522/14; 522/28; 522/73; 522/77; 522/81; 522/82; 522/83; 522/181; 522/908; 523/116; 524/417; 524/494

[58] Field of Search ............... 522/14, 81, 82, 908; 523/116

[56] References Cited

U.S. PATENT DOCUMENTS 4,224,072 9/1980 Stewart ............................. 522/2
4,437,836 3/1984 Schmitz-Josten ................. 522/14
4,674,980 6/1987 Ibsen .................................. 522/14

OTHER PUBLICATIONS

Dentsply International "VLC Dycal" Dentsply International markets a product under the trademark VLC Dycal which is a dental cavity liner material, (1980).

Primary Examiner—John C. Bleutge
Assistant Examiner—David Buttner
Attorney, Agent, or Firm—Marjama & Pincelli

[57] ABSTRACT

A visible light activated cavity liner which provides an available source of leachable calcium and fluoride to the base of a tooth cavity, said composition comprising a photopolymerizable matrix material, a photo initiator, a reducing agent, a synthetic hydroxyapatite filler and a powdered glass ionomer filler.

5 Claims, No Drawings

VISIBLE LIGHT ACTIVATED CAVITY LINER

BACKGROUND OF THE INVENTION

The present invention is directed to a light activated cavity liner for use in the dental field.

Calcium hydroxide has been widely used as the basis of many cavity liners and bases for at least the past four decades and it is commonly believed that the presence of calcium ions stimulates the formation of reparative dentine at the base of tooth cavities, thus aiding the natural healing process. Additionally these calcium hydroxide based cavity liners and bases help to protect the pulp of the tooth from any leachable constituent of dental filling materials used to fill the cavity.

In recent years, however, there is increasing evidence that suggests that the prevention of microleakage around a tooth restoration and through the base of a cavity to the pulp is a prime requisite for rapid and successful healing and prevention of secondary or recurrent caries.

Also during recent years there has been a large increase in the use of light curable, particularly visible light curable, dental restorative materials as the versatility and esthetic potential of these materials has become apparent and widely recognized.

Very recently a visible light curable cavity base or liner composition based on calcium hydroxide has been commercially developed. Although this material is a single component version, requiring no mixing, and is curable with a standard composite restorative curing light, there are many ways in which it can be improved to more nearly approach the idealized material indicated by current restorative and histological research. These aspects will be explained in detail in the following summary of the invention.

SUMMARY OF THE INVENTION

The visible light activated cavity liner of the present invention comprises a photopolymerizable matrix material, a photoinitiator, a reducing agent, a synthetic hydroxyapatite filler and a powdered basic fluoro-alumino silicate glass filler. The basic ingredients are usually supplemented with a radiopaquing agent(s) to facilitate radiographic detection of the material in vivo, an adhesion promoter to enhance adhesion to tooth structure, pigment(s) to confer tooth shading to the material, and optionally a thickener(s) to reduce the tendency of paste separation during storage prior to use.

A review of current dental restorative and histological research indicates the following requirements for the idealized cavity base or liner material.
1. Availability of leachable calcium.
2. Availability of leachable fluoride to minimize the formation of secondary caries.
3. Minimize microleakage, by providing as impervious a protective barrier as possible.
4. More radiopaque than tooth structure for radiographic differentiation.
5. Sufficiently hydrophilic to adequately wet dentine in vivo.
6. Capability for bonding to both dentine and composite dental restorative materials.
7. Natural Dentine appearance.
8. Capability for offshade dentine matching.
9. Optimized placement consistency.
10. Readily curable with a standard visible light curing unit.
11. Extremely resistant to standard acid etchants.
12. Near neutral ph for maximum healing potential.
13. Excellent pulpal histology.
14. Extremely low solubility and disintegration.
15. Non-bioresorbable.

The above and other objectives are accomplished in accordance with the present invention as more fully described in the following detailed description.

DETAILED DESCRIPTION OF THE INVENTION

The essential components of the visible light activated cavity liner of the present invention comprises a photopolymerizable matrix material, a photoinitiator, a reducing agent, synthetic hydroxyapatite filler and a powdered basic fluoro-alumino silicate filler. More specifically the various components of the present invention comprise the following:

A low toxicity acrylic functional resin binder such as Ethoxylated Bisphenol A Dimethacrylate, the adduct of Bisphenol A and Glycidyl Methacrylate known as BisGMA, or blends of either one with Bisphenol A Dimethacrylate is preferred.

A hydrophilic comonomer diluent such as Hydroxyethyl methacrylate or Hydroxpropyl methacrylate, though other hydroxyl functional comonomers can also be used.

Synthetic hydroxyapatite, $3Ca_3(PO_4)_2.Ca(OH)_2$, is used as a filler containing leachable calcium ions, although calcium hydroxide or calcium oxide, or many other calcium containing compounds or minerals, could be optionally substituted for the synthetic hydroxyapatite.

Commercially available glass powder sold for dental use is used as a filler containing leachable fluoride ions. This material comprises basic fluoro-alumino silicate glasses. These glass powders are also referred to in the dental art as powders for use in glass ionomer cements. There are many available sources of this material. A suitable material is available from Espe of Germany under the tradename "Ketac" powder. Another suitable basic fluoro-alumino silicate glass powder has the following approximate composition by weight and is available from Industrial Corp. of Glenmoore, Pa. and identified as IG-91-2589:
 silicon dioxide: 31
 aluminum oxide: 24
 sodium aluminum fluoride: 18
 aluminum phosphate: 15
 aluminum fluoride: 12.

A high level of radiopacity is conferred to the subject material by the inclusion of a major proportion of barium sulfate as a third filler component, though other radiopaquing agents such as barium tungstate or barium aluminum borosilicate may be optionally substituted. Capability for adhesion to a prepared dentine substrate is provided by the inclusion of an organofunctional silane such as Methacryloxypropyl trimethoxysilane, although other materials could also be substituted.

Dentine like pigmentation is achieved by the incorporation of suitable particulate pigments such as iron oxides, animal charcoal or other equivalent material.

A combination of a photoreactive diketone and a synergistic tertiary amine reducing agent, preferably acrylic functional, is used as a photosensitizing couplet, although any photosensitizing system which will function effectively when the material is exposed to a high intensity dental radiation source of about 375–550 nanometer wavelength output may be substituted.

Typical photosensitizers include benzophenone, acetophenone, thioxanthen-9one, 9-fluorenone, antharaquinone, 4'methoxyacetophenone, diethoxyacetophenone and the diketones, such as biacetyl, 2,3 pentanedione, benzil, 4,4'methoxybenzil, 4,4'oxidibenzil, and dl camphroquinone. Camphroquinone and diketones absorb mostly in the visible light spectrum between 400 and 500 nanometers. Formulations with these initiators cure readily with visible radiation.

The dental impression materials also contain a reducing agent which reduces the ketonic photosensitizers when they are in the excited state and accelerates the rate of polymerization. These materials comprise organic amines, aliphatic or aromatic, monoamines, or polyamines, primary, secondary or tertiary. Diethylaminoethyl methacrylate is a typical material. The tertiary amines are generally preferred. Suitable tertiary amines are described U.S. Pat. No. 3,759,807 which is incorporated herein by reference. Tertiary amines with additional functional groups are also employed such as 4,4'bis(dimethylamino)benzophenone, N-methyldiethanolamine, 4 dimethylaminobenzoate, dimethylaminobenzaldehyde, di-methylaminoethylmethacrylate and dimethylaminoethylacrylate.

The following examples illustrate the broad and preferred concentration ranges for formulations of the present invention. All percentages are by weight.

EXAMPLE 1

| BROAD FORMULATION | BROAD CONCENTRATION |
|---|---|
| Ethylenically unsaturated resin | 15–60 |
| Radiopaquing agent | 10–50 |
| Basic Fluoro-Alumino Silicate Glass powder | 5–30 |
| Synthetic hydroxyapatite | 5–30 |
| Hydrophilic ethylenically unsaturated diluent | 2–20 |
| Pigment blends | 0.2–10.0 |
| Polymerizable adhesion promoter | 0.1–2.0 |
| Synergistic amine reducing agent | 0.05–2.0 |
| Visible light photosensitizer | 0.01–2.0 |

EXAMPLE 2

|  | BROAD CONCENTRATION | PREFERRED RANGE |
|---|---|---|
| Ethoxylated Bisphenol A Dimethacrylate | 15–60 | 25–40 |
| Barium Sulfate | 10–50 | 20–25 |
| Basic Fluoro-Alumino Silicate Glass Powder | 5–30 | 10–20 |
| Synthetic Hydroxyapatite | 5–30 | 10–20 |
| Hydroxyethyl Methacrylate | 2–20 | 4–10 |
| Yellow iron oxide pigment blend (Fe₂O₃) | 0.1–5.0 | 1–3 |
| Gray animal charcoal/T₁O₂ pigment blend | 0.1–5.0 | 1–3 |
| Methacryloxypropyltrimethoxy Silane | 0.1–5.0 | 0.5–2.0 |
| Tertiary Amine reducing agent | 0.05–2.0 | 0.1–1.0 |
| α Diketone photosensitizer | 0.01–2.0 | 0.05–1.0 |

A specific example of one embodiment of the present invention is as follows:

EXAMPLE 3

|  | WT. PERCENT |
|---|---|
| Ethoxylated Bisphenol A Dimethacrylate | 17.0 |
| Bisphenol A Dimethacrylate | 17.0 |
| Hydroxy Propyl Methacrylate | 7.5 |
| Barium Aluminum Borosilicate | 24.0 |
| Synthetic Hydroxyapatite | 16.0 |
| Basic Fluoro-Alumino Silicate Glass Powder | 16.0 |
| Diethylaminoethylmethacrylate | 0.5 |
| Benzil | 0.5 |
| Methacryloxypropyltrimethoxy Silane | 1.0 |
| Pigments | 0.5 |

All of the ingredients which make up compositions of the present invention may be used within the stated preferred ranges, advantageously towards the midpoint of these ranges, in virtually any chosen combination with a good measure of success, since by their intended end use these materials are only required to be used in relatively thin layers, up to a maximum of about one millimeter thickness, which are readily curable.

The following is a typical method used in preparing formulations of the present invention, though other methods known to the arts may also be used:

In a closed area of filtered light below 550 nanometers wavelength the following ingredients are blended together in a double planetary mixer in the stated order:

| Ethoxylated Bisphenol A. Dimethacrylate (liquid) | 32.0 |
|---|---|
| Hydroxyethyl Methacrylate (liquid) | 6.6 |
| Dimethylaminoethyl methacrylate (liquid) | 0.55 |
| Methacryloxypropyltrimethoxy Silane (liquid) | 1.0 |
| 2,3 - Bornenedione (soluble solid) | 0.45 |
| Yellow Pigment Blend (paste) | 2.0 |
| Gray Pigment Blend (paste) | 2.0 |
| Synthetic Hydroxyapatite (solid) | 15.0 |
| *Basic Fluoro-Alumino Silicate Glass Powder (solid) | 15.0 |
| Barium Sulfate (solid) | 22.5 |
| Sub-micron Silica (solid) | 3.0 |

*IG-91-2589; Industrial Corp.; Glenmoore, PA

The resulting thixotropic paste of 30,000±5% centiposes viscosity is then rollmilled to maximize homogenity, followed by packaging in lightproof containers. A sample of the rollmilled paste is tested for performance by placing in a circular Teflon mold of 6.5 millimeters diameter and 1.5 millimeters depth, laid on a microscope slide backed by white paper. The mold is closed by squeezing the excess paste out with a second microscope slide and the paste is then exposed to a visible light source of approximately 15,000 microwatts per square centimeter intensity, for a time of 20 seconds, at a range or distance of one centimeter. The cured specimen is demolded by moving the two microscope slides carefully in opposite directions to break the surface seals and tested for hardness with a Barber-Coleman hardness tester. Top/Bottom readings of 90/85±2 should be obtained if the material has been satisfactorily formulated.

Physical properties of the actual material used in the monkey histology tooth cavity placement study are as follows, together with comparative test data for the only existing visible light curable cavity base or liner composition, based on calcium hydroxide, and data for a typical dental glass ionomer base or liner material:

TABLE

|  | MATERIAL OF INVENTION EXAMPLE 4 | COMMERCIAL CAVITY LINER MATERIAL* | COMMERCIAL CAVITY LINER MATERIAL** |
|---|---|---|---|
| Form: | Single Paste | Single Paste | Powder/Liquid |
| Proportioning: | None | None | 1.3 to 1 by weight |
| Mixing: | None | None | 40 secs. |
| PH: | 6.5 | 9.5 | 2.0 (as mixed) |
| Work Time: | As desired up to 5 min. | Up to 4 min | 3 mins. |
| Set Time: | 20 seconds | 20 seconds | 6 mins. |
| Compressive Strength (24 hrs): | 29,500 PSI | 13,500 PSI | 18,000 PSI |
| Diametral Tensile Strength (24 hrs): | 2250 PSI | <2000 PSI | 1960 PSI |
| Water Solubility (7 days): | 0.21% | 0.5% | 0.35% |
| Fluoride Release (21 days): | >2900 Micrograms | NIL | 1800 Micrograms |
| Calcium Content: | 5.92% | 8% | 9.44% |
| Form of Calcium: | Hydroxyapatite | Calcium Hydroxide | Basic Glass |
| Calcium Release (7 days): | 0.206% | >0.2% | None Detectable |
| Radiopacity: | Good | Fair | Fair |
| Resistance to 37.5% Phosphoric Acid | No Change | <0.18% Sol. | Etched |

*Light cured calcium hydroxide cavity liner sold by Dentsply under the tradename "DYCAL".
**A glass ionomer cavity liner available from GC International (Japan) under the tradename GC GIASS Ionomer Lining Cement.

It will be readily seen from the data in the above TABLE that the material of the present invention has a physiologically neutral pH, superior strength properties when cured, lower water solubility, and provides a source of leachable calcium and fluoride ions. Further, it has excellent resistance to 37% phosphoric acid which is customerily used to etch the cavo surface margins of tooth cavities to enhance bond strength to composite restorative materials, and is truly radioopaque.

Although particular embodiments of the present invention have been disclosed herein for purposes of explanation, further modifications or variations thereof will be apparent to those skilled in the art to which this invention pertains.

What is claimed is:

1. A visible light activated cavity liner in the form of a low viscosity paste which provides an available source of leachable calcium and fluoride to the base of a tooth cavity, said composition comprising a photopolymerizable matrix material, a photoinitiator, a reducing agent, a synthetic hydroxyapatite filler and a powdered basic fluoro-alumino silicate glass filler, with said paste prior to photopolymerization, being capable of wetting and chemically bonding to tooth structure, and after photopolymerization being capable of bonding to composite restorative material used to complete the filling of a dental cavity.

2. A visible light activated cavity liner in the form of a paste which comprises in weight percent:

| Ethoxylated Bisphenol A Dimethacrylate | 15-60 |
|---|---|
| Barium Sulfate | 10-50 |
| Basic Fluoro-Alumino Silicate Glass Powder | 5-30 |
| Synthetic Hydroxyapatite | 5-30 |
| Hydroxyethyl Methacrylate | 2-20 |
| Yellow Pigment Blend | 0.1-5.0 |
| Gray Pigment Blend | 0.1-5.0 |
| Methacryloxypropyltrimethoxy Silane | 0.1-5.0 |
| Tertiary Amine Reducing Agent | 0.05-2.0 |
| α Diketone Photosensitizer | 0.01-2.0 | with said paste, prior to photopolymerization being capable of wetting and chemically bonding to tooth structure, and after photopolymerization being capable of bonding to composite restorative material used to complete the filling of a dental cavity.

3. A visible light activated cavity liner in the form of a paste which comprises in weight percent:

| Ethoxylated Bisphenol A Dimethacrylate | 25-40 |
|---|---|
| Barium Sulfate | 20-25 |
| Basic Fluoro-Alumino Silicate Glass Powder | 10-20 |
| Synthetic Hydroxyapatite | 10-20 |
| Hydroxyethyl Methacrylate | 4-10 |
| Yellow Pigment Blend | 1-3 |
| Gray Pigment Blend | 1-3 |
| Methacryloxypropyltrimethoxy Silane | 0.5-2.0 |
| Tertiary Amine Reducing Agent | 0.1-1.0 |
| α Diketone Photosensitizer | 0.05-1.0 | with said paste, prior to photopolymerization being capable of wetting and chemically bonding to tooth structure, and after photopolymerization being capable of bonding to composite restorative material used to complete the filling of a dental cavity.

4. A visible light activated cavity liner in the form of a paste comprises in weight percent:

| Ethoxylated Bisphenol A Dimethacrylate | 17.0 |
|---|---|
| Bisphenol A Dimethacrylate | 17.0 |
| Hydroxy Propyl Methacrylate | 7.5 |
| Barium Aluminum Borosilicate | 24.0 |
| Synthetic Hydroxyapatite | 16.0 |
| Basic Fluoro-Alumino Silicate Glass Powder | 16.0 |
| Diethylaminoethylmethacrylate | 0.5 |
| Benzil | 0.5 |
| Methacryloxypropyltrimethoxy Silane | 1.0 |
| Pigments | 0.5 | with said paste prior to photopolymerization, being capable of wetting and chemically bonding to tooth structure, and after photopolymerization being capable of bonding to composite restorative material used to complete the filling of a dental cavity.

5. A visible light activated cavity liner in the form of a paste which comprises in weight percent:

| Ethylenically Unsturated Resin | 15-60 |
|---|---|
| Radiopaquing Agent | 10-50 |
| Basic Fluoro-Alumino Silicate Glass Powder | 5-30 |
| Synthetic Hydroxyapatite | 5-30 |

| -continued | |
|---|---|
| Hydrophilic Ethylenically Unsaturated Diluent | 2–20 |
| Pigment Blends | 0.2–10.0 |
| Polymerizable Adhesion Promoter | 0.1–2.0 |
| Synergistic Amine Reducing Agent | 0.05–2.0 |
| Visible Light Photosensitizer | 0.01–2.0 | with said paste prior to photopolymerization being capable of wetting and chemically bonding to tooth structure, and after photopolymerization being capable of bonding to composite restorative materials used to complete the filling of a dental cavity.

* * * * *